United States Patent
Campbell et al.

(10) Patent No.: US 7,153,692 B2
(45) Date of Patent: Dec. 26, 2006

(54) DIAGNOSTIC METHODS FOR DETERMINING SUSCEPTIBILITY TO CONVULSIVE CONDITIONS

(75) Inventors: Allyson J. Campbell, Kingston (CA); Donald F. Weaver, Halifax (CA); Angela P. Lyon, Kingston (CA); John R. Carran, Kingston (CA)

(73) Assignee: Queens University at Kingston, Kingston (CA)

( * ) Notice: Subject to any disclaimer, the term of this patent is extended or adjusted under 35 U.S.C. 154(b) by 0 days.

(21) Appl. No.: 11/106,369

(22) Filed: Apr. 13, 2005

(65) Prior Publication Data
US 2006/0008917 A1  Jan. 12, 2006

Related U.S. Application Data

(63) Continuation of application No. 10/222,957, filed on Aug. 16, 2002, now abandoned.

(60) Provisional application No. 60/378,781, filed on May 7, 2002, provisional application No. 60/318,139, filed on Sep. 7, 2001.

(51) Int. Cl.
*G01N 33/00* (2006.01)
(52) U.S. Cl. ............................. 436/90; 436/63; 436/86; 436/89; 436/161; 73/61.52; 73/61.55; 210/656
(58) Field of Classification Search ................. 436/63, 436/86, 89, 90, 161, 174, 175, 177; 73/61.52, 73/61.55; 210/656; 514/561
See application file for complete search history.

(56) References Cited

U.S. PATENT DOCUMENTS

| | | | |
|---|---|---|---|
| 4,474,888 A | 10/1984 | Gindler et al. | |
| 5,995,868 A * | 11/1999 | Dorfmeister et al. | 600/544 |
| 6,451,761 B1 | 9/2002 | van Gelder et al. | |
| 2003/0114441 A1 | 6/2003 | Weaver et al. | |

OTHER PUBLICATIONS van Gennip et al. Clinical Chemistry, vol. 39, No. 3, 1993, pp. 380-385.*
De Guevara et al. Journal of Chromatography, vol. 528, 1990, pp. 35-41.*
Abe T, et al. High-performance liquid chromatographic determination of beta-alanine, beta-aminoisobutyric acid and gamma-aminobutyric acid in tissue extracts and urine of normal and (aminooxy)acetate-treated rats. J Chromatogr B Biomed Sci Appl. Aug. 7, 1998;712(1-2):43-9.
Araki K, et al. Alteration of amino acid content of cerebrospinal fluid from patients with epilepsy. Acta Neurol Scand. Dec. 1988;78(6):473-9.
Bakkeren JAJM, et al. Elevated urine, blood and cerebrospinal fluid levels of uracil and thymine in a child with dihydrothymine dehydrogenase deficiency. Clin Chim Acta. Jul. 31, 1984;140(3):247-56.
Beyer C, et al. Prevention of the convulsant and hyperalgesic action of strychnine by intrathecal glycine and related amino acids. Pharmacol Biochem Behav. Jan. 1988;29(1):73-8.
Braakhekke JP, et al. Dihydropyrimidine dehydrogenase deficiency. Neurological aspects. J Neurol Sci. Mar. 1987;78(1):71-7.
Carducci C, et al. Automated method for the measurement of amino acids in urine by high-performance liquid chromatography. J Chromatogr A. Apr. 5, 1996;729(1-2):173-80.
Choquet D, et al. Does beta-alanine activate more than one chloride channel associated receptor? Neurosci Lett. Feb. 3, 1988;84(3):329-34.
Crawford PM, et al. GABA and amino acid concentrations in lumbar CSF in patients with treated and untreated epilepsy.Epilepsy Res. Nov.-Dec. 1987;1(6):328-38.
Curtis DR, et al. A pharmacological study of the depression of a spinal neurones by glycine and related amino acids. Exp Brain Res. 1968;6(1):1-18.
Curtis DR, et al. Antagonism between bicuculline and GABA in the cat brain. Brain Res. Oct. 8, 1971;33(1):57-73.
Curtis DR, et al. Bicuculline, an antagonist of GABA and synaptic inhibition in the spinal cord of the cat. Brain Res. Sep. 10, 1971;32(1):69-96.
Davidson DLW, et al. Ouabain induced seizures: site of production and response to anticonvulsants. Can J Neurol Sci. Nov. 1978;5(4):405-11.
De Abreu RA, et al. High-performance liquid chromatographic determination of purine and pyrimidine bases, ribonucleosides, deoxyribonucleosides and cyclic ribonucleotides in biological fluids. J Chromatogr. Apr. 16, 1982;229(1):67-75.
DeFeudis FV, et al. Is Beta-alanine an inhibitory neurotransmitter? Gen Pharmacol. 1977;8(3):177-80.
del Rio RM, et al. Contents of beta-alanine and gamma-aminobutyric acid in regions of rat CNS.Exp Brain Res. Jun. 27, 1977;28(3-4):225-7.
Devinsky O, et al. Cerebrospinal fluid levels of neuropeptides, cortisol, and amino acids in patients with epilepsy. Epilepsia. Mar.-Apr. 1993;34(2):255-61.
Deyl Z, et al. Profiling of amino acids in body fluids and tissues by means of liquid chromatography. J Chromatogr. Jun. 20, 1986;379:177-250.

(Continued)

*Primary Examiner*—Maureen M. Wallenhorst
(74) *Attorney, Agent, or Firm*—Davidson, Davidson & Kappel

(57) ABSTRACT

The present invention exploits the discovery that amounts of uracil and thymine metabolites, especially β-aminoisobutyric acid, in various bodily fluids, especially urine, are correlated with the occurrence of epilepsy when compared to matched control subjects. Analytical and diagnostic protocols, including a novel high performance liquid chromatography system, for use in the invention are disclosed.

21 Claims, 2 Drawing Sheets

OTHER PUBLICATIONS

Fariello RG. Action of inhibitory amino acids on acute epileptic foci: an electrographic study. Exp Neurol. Oct. 1979;66(1):55-63.

Ferrie CD, et al. Plasma amino acids in childhood epileptic encephalopathies. Epilepsy Res. Apr. 1999;34(2-3):221-9.

Fürst P, et al. Appraisal of four pre-column derivatization methods for the high-performance liquid chromatographic determination of free amino acids in biological materials. J Chromatogr. Jan. 19, 1990;499:557-69.

Gardner WS, et al. Reverse-phase liquid chromatographic analysis of amino acids after reaction with o-phthalaldehyde. Anal Biochem. Jan. 1, 1980;101(1):61-5.

Georgi G, et al. High-performance liquid chromatographic determination of amino acids in protein hydrolysates and in plasma using automated pre-column derivatization with o-phthaldialdehyde/2-mercaptoethanol. J Chromatogr. Mar. 5, 1993;613(1):35-42.

Gonzalez FJ, et al. Diagnostic analysis, clinical importance and molecular basis of dihydropyrimidine dehydrogenase deficiency. Trends Pharmacol Sci. Oct. 1995;16(10):325-7.

Grove J, et al. Increased gamma-aminobutyric acid (GABA), homocarnosine and beta-alanine in cerebrospinal fluid of patients treated with gamma-vinyl GABA (4-amino-hex-5-enoic acid). Life Sci. May 21, 1981;28(21):2431-9.

Gusel VA, et al. [Effect of GABA-positive substances on the primary and mirror epileptogenic foci in the hippocampus of rats] Farmakol Toksikol. May-Jun. 1986;49(3):96-100.

Haines JL, et al. Altered amino acid levels in multiply affected sibships with seizures. Epilepsia. Nov.-Dec. 1985;26(6):642-8.

Hamberger A, et al. Nico M. van Gelder, the inquisitive neurochemist. Neurochem Res. Nov. 1999;24(11):1321-4.

Higgins JJ, et al. Pyridoxine-responsive hyper-beta-alaninemia associated with Cohen's syndrome. Neurology. Sep. 1994;44(9):1728-32.

Holopainen I, et al. High-affinity uptake of taurine and beta-alanine in primary cultures of rat astrocytes. Neurochem Res. Feb. 1986;11(2):207-15.

Horikoshi T, et al. Taurine and beta-alanine act on both GABA and glycine receptors in Xenopus oocyte injected with mouse brain messenger RNA. Brain Res. Sep. 1988;464(2):97-105.

Hosli E, et al. Cellular localization of the uptake of [$^3$H]taurine and [$^3$H]beta-alanine in cultures of the rat central nervous system. Neuroscience. 1980;5(1):145-52.

Iinuma K, et al. Hyperamino-acidaemia and hyperammonaemia in epileptic children treated with valproic acid. Eur J Pediatr. Dec. 1988;148(3):267-9.

Jaeken J, et al. Gamma-vinyl GABA, and GABA and beta-alanine transamination. The Lancet. Mar. 31, 1984; 323:737.

Jacobs WA, et al. Stability of o-phthalaldehyde-derived isoindoles. Anal Biochem. Aug. 1, 1986;156(2):334-40.

Jarrett HW, et al. The separation of o-phthalaldehyde derivatives of amino acids by reversed-phase chromatography on octylsilica columns. Anal Biochem. Feb. 15, 1986;153(1):189-98.

Jones BN, et al. o-Phthaldialdehyde precolumn derivatization and reversed-phase high-performance liquid chromatography of polypeptide hydrolysates and physiological fluids. J Chromatogr. Aug. 26, 1983;266:471-82.

Kawamura H, et al. Depression of cerebellar Purkinje cells by microiontophoretic application of GABA and related amino acids. Brain Res. Dec. 1, 1970;24(2):293-304.

Kihara M, et al. Release by electrical stimulation of endogenous glutamate, gamma-aminobutyric acid, and other amino acids from slices of the rat medulla oblongata. J Neurochem. Jan. 1989;52(1):261-7.

Kontro P. Beta-alanine uptake by mouse brain slices. Neuroscience. Jan. 1983;8(1):153-9.

Lahat E, et al. Aminoaciduria resulting from vigabatrin administration in children with epilepsy. Pediatr Neurol. Jul. 1999;21(1):460-3.

Larsson OM, et al. Mutual inhibition kinetic analysis of gamma-aminobutyric acid, taurine, and beta-alanine high-affinity transport into neurons and astrocytes: evidence for similarity between the taurine and beta-alanine carriers in both cell types. J Neurochem. Aug. 1986;47(2):426-32.

Lopez-Colome AM, Taurine receptors in CNS membranes: binding studies. Adv Exp Med Biol. 1981;139:293-310.

Martin DL, et al. High affinity transport of taurine and beta-alanine and low affinity transport of gamma-aminobutyric acid by a single transport system in cultured glioma cells. J Biol Chem. Aug. 10, 1979;254(15):7076-84.

McBride WJ, et al. Contents of several amino acids in the cerebellum, brain stem and cerebrum of the 'staggerer', 'weaver' and 'nervous' neurologically mutant mice. J Neurochem. May 1976;26(5):867-70.

Monaco F, et al. Free amino acids in serum of patients with epilepsy: significant increase in taurine. Epilepsia. Jun. 1975;16(2):245-9.

Monaco F, et al. Plasma aminoacid alterations in idiopathic generalized epilepsy: an investigation in probands and their first-degree relatives. Ital J Neurol Sci. Apr. 1994;15(3):137-44.

Morineau G, et al. Reaction of o-phthalaldehyde with amino acids and glutathione. Application to high-performance liquid chromatography determination. J Chromatogr. Apr. 21, 1989;467(1):209-16.

Mutani R, et al. Free amino acids in the cerebrospinal fluid of epileptic subjects. Epilepsia. Dec. 1974;15(4):593-7.

Nadi NS, et al. Distribution of several amino acids in regions of the cerebellum of the rat. J Neurochem. Feb. 1977;28(2):453-5.

Oja SS, et al. Modification of chloride flux across brain membranes by inhibitory amino acids in developing and adult mice. Neurochem Res. Aug. 1990;15(8):797-804.

Okajima K, et al. A screening method for dihydropyrimidine dehydrogenase deficiency with colorimetric detection of urinary uracil. Adv Exp Med Biol. 1989;253A:119-22.

Okamoto K, et al. Action of amino acids and convulsants on cerebellar spontaneous action potentials in vitro: effects of deprivation of $Cl^{31}$, $K^+$ of $Na^+$. Brain Res. Aug. 20, 1976;113(1):147-58.

Parker I, et al. Responses to GABA, glycine and beta-alanine induced in Xenopus oocytes by messenger RNA from chick and rat brain. Proc R Soc Lond B Biol Sci. Mar. 22, 1988;233(1271):201-16.

Perry TL, et al. The amino acid content of human cerebrospinal fluid in normal individuals and in mental defectives. J Clin Invest. Aug. 1961;40:1363-72.

Pitkänen A, et al. Effect of vigabatrin (gamma-vinyl GABA) on amino acid levels in CSF of epileptic patients. J Neurol Neurosurg Psychiatry. Nov. 1988;51(11):1395-400.

Plum CM. Free amino acid levels in the cerebrospinal fluid of normal humans and their variation in cases of epilepsy and Spielmeyer-Vogt-Batten disease. J Neurochem. Sep. 1974;23(3):595-600.

Qureshi GA, et al. Application of high-performance liquid chromatography to the determination of the free amino acids in physiological fluids. J Chromatogr. Aug. 3, 1984;297:91-100.

Riddall DR, et al. Neurotransmitter uptake into slices of rat cerebral cortex in vitro: effect of slice size. J Neurochem. Oct. 1976;27(4):835-9.

Roth M. Fluorescence reaction for amino acids. Anal Chem. Jun. 1971;43(7):880-2.

Rowley HL, et al. Determination of in vivo amino acid neurotransmitters by high-performance liquid chromatography with o-phthalaldehyde-sulphite derivatisation. J Neurosci Methods. Mar. 1995;57(1):93-9.

Sandberg, M. et al. Beta-alanine, a possible neurotransmitter in the visual system? J Neurochem. 1981; 37(5):1353-1356.

Sangiah S. Effects of glycine and other inhibitory amino acid neurotransmitters on strychnine convulsive threshold in mice. Vet Hum Toxicol. Apr. 1985;27(2):97-9.

Saransaari P, et al. Uptake and release of beta-alanine in cerebellar granule cells in primary culture: regulation of release by glutamatergic and GABAergic receptors. Neuroscience. Mar. 1993;53(2):475-81.

Sarwar G, et al. Evaluation of liquid chromatographic analysis of nutritionally important amino acids in food and physiological samples. J Chromatogr. May 19, 1993;615(1):1-22.

Schechter PJ, et al. Gamma-vinyl GABA, and GABA and beta-alanine transamination. The Lancet. Mar. 31, 1984; 323:737-38 [response to Jaeken].

Scriver CR, et al. Hyper-beta-alaninemia associated with beta-aminoaciduria and gamma-aminobutyricaciduria, somnolence and seizures. N Engl J Med. Mar. 24, 1966:274(12):635-643.

Seiler N, et al. Synergistic anticonvulsant effects of GABA-T inhibitors and glycine. Naunyn Schmiedeberg's Arch Pharmacol. May 1984;326(1):49-57.

Severini G, et al. Biochemical indices of renal damage: separation of urinary alanine aminopeptidase by liquid chromatography. J Chromatogr. OCt. 30, 1987;421(2):344-9.

Shih VE, et al. Aminoaciduria due to vinyl-GABA administration. N Engl J Med. Nov. 8, 1990;323(19):1353.

Simons SS, et al. Reaction of o-phthalaldehyde and thiols with primary amines: formation of 1-alkyl (and aryl) thio-2-alkylisoindoles. J Org Chem. 1978:43(14):2886-91.

Simons SS, et al. The structure of the fluorescent adduct formed in the reaction of o-phthalaldehyde and thiols with amines. J Am Chem Soc. 1976:98(22):7098-7099.

Smolders I, et al. The analysis of excitatory, inhibitory and other amino acids in rat brian microdialysates using microbore liquid chromatography. J Neurosci Methods. Mar. 1995;57(1):47-53.

Sumi S, et al. Automated screening system for purine and pyrimidine metabolism disorders using high-performance liquid chromatography. J Chromatogr B Biomed Appl. Oct. 20, 1995;672(2):233-9.

Sur RN, et al. Some central actions of beta-alanine. Indian J Exp Biol. Aug. 1977;15(8):634-8.

Teerlink T, et al. Plasma amino acids determined by liquid chromatography within 17 minutes. Clin Chem. Feb. 1994;40(2):245-9.

Toggenburger G, et al. *In vitro* release of endogenous beta-alanine, GABA, and glutamate, and electrophysiological effect of beta-alanine in pigeon optic tectum. J Neurochem. Jul. 1982;39(1):176-83.

Tuchman M, et al. Familial pyrimidinemia and pyrimidinuria associated with severe fluorouracil toxicity. N Engl J Med. Jul. 25, 1985;313(4):245-9.

Turnell D.C. et al. Rapid assay for amino acids in serum or urine by pre-column derivatization and reversed-phase liquid chromatography. Clin Chem. 1982; 28(3):527-31.

Valik D, et al. Hereditary disorders of purine and pyrimidine metabolism: identification of their biochemical phenotypes in the clinical laboratory. Mayo Clin Proc. Aug. 1997;72(8):719-25.

van Gelder NM, et al. Amino acid content of epileptogenic human brain: focal versus surrounding regions. Brain Res. May 26, 1972;40(2):385-93.

van Gelder NM, et al. Plasma amino acids in 3/sec spike-wave epilepsy. Neurochem Res. Jun. 1980;5(6):659-71.

van Gennip AH, et al. Comparative study of thymine and uracil metabolism in healthy persons and in a patient with dihydropyrimidine dehydrogenase deficiency. Adv Exp Med Biol. 1989;253A:111-8.

Vásquez-Ortiz F.A. et al. High performance liquid chromatographic determination of free amino acids in shrimp. J Liquid Chromatogr. 1995; 18(10):2059-68.

Zafra F, et al. beta-Alanine transport into plasma membrane vesicles derived from rat brain synaptosomes. Neurochem Res. May 1984;9(5):695-707.

* cited by examiner

FIGURE 2

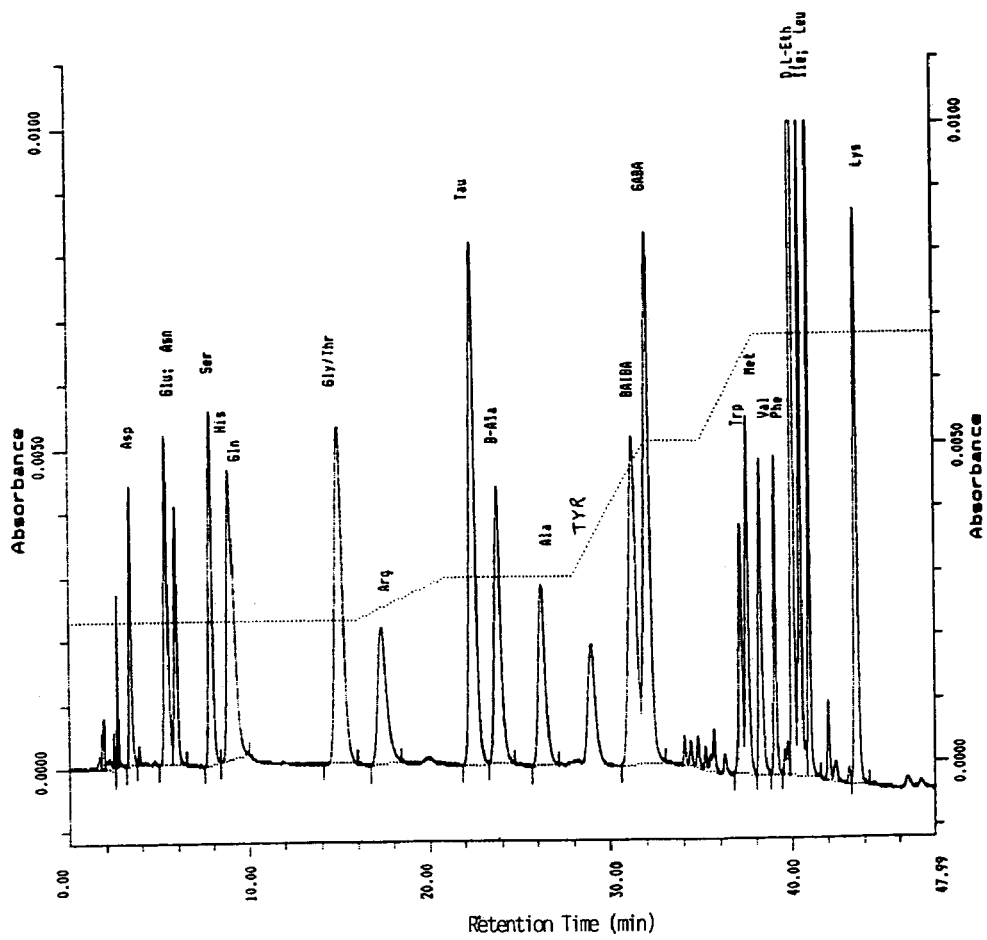

Abbreviations: Asp = Aspartic Acid, Glu = Glutamic Acid, Asn = Asparagine, Ser = Serine, His = Histamine, Gln = Glutamine, Gly = Glycine, Thr = Threonine, Arg = Arginine, Tau = Taurine, B-Ala = β-Alanine, Ala = Alanine, Tyr = Tyrosine, BAIBA = β-Aminoisobutyric Acid, GABA = γ-Aminobutyric Acid, Trp = Tryptophan, Met = Methionine, Val = Valine, Phe = Phenylalanine, D,L-Eth = D,L-Ethionine, Ile = Isoleucine, Leu = Leucine, Lys = Lysine.

DIAGNOSTIC METHODS FOR DETERMINING SUSCEPTIBILITY TO CONVULSIVE CONDITIONS

RELATED APPLICATIONS

This application is a continuation of U.S. patent application Ser. No. 10/222,957, filed Aug. 16, 2002, now abandoned, which claims the priority of U.S. provisional patent application 60/318,139, filed Sep. 7, 2001, and U.S. provisional patent application 60/378,781, filed May 7, 2002. The entire contents of each of the foregoing patent applications are hereby expressly incorporated herein by reference in their entirety.

BACKGROUND OF THE INVENTION

A variety of clinical methods exist by which a physician is directed to a diagnosis of the cause of apparent seizures in a patient as either epilepsy or otherwise. For example, routine blood studies including electrolyte and glucose measurements, complete blood counts, and toxin screens may be carried out to assist a physician in determining a cause of seizures in a patient. Medical imaging, including CT and MRI, as well as EEG examinations may also yield valuable clinical information in this regard. There are, however, no routinely used prospective or predictive clinical tests which a physician may perform which indicate whether or not a patient is at risk of developing seizures in the future.

Retrospective studies have revealed that several factors are associated with an increased risk of seizure, for example, a familial history of seizures, meningitis, or a recent head trauma. An individual's susceptibility to seizure is determined additionally by the individual's brain chemistry, and consequently a head trauma of equal magnitude, e.g., may precipitate seizures in one individual, but not another. Presently, there is no predictive test to distinguish between these two hypothetical individuals.

To the contrary, following head trauma or insult to the brain it is common practice to administer prophylactically anti-seizure drugs to most patients who fall into an "at risk" category, without any analysis of the individual's actual risk. Accordingly, patients who are at lower risk of developing seizures are subjected to the unnecessary side-effects of various drugs, such as, e.g., inhibition of neuroplasticity. A need remains, therefore, for a predictive test which more accurately indicates a patient's actual risk of developing seizures.

Distinguishing pseudoseizures from seizures is another clinical need that such a test may address. Pseudoseizures are seizure-like spells with no physiological basis. They can either be intentionally or subconsciously induced. The treatment for pseudoseizures is often psychological in nature, and patients undergo unnecessary effects if anticonvulsant medication is administered due to a misdiagnosis.

Although epileptic seizures are rarely fatal, large numbers of patients require medication to avoid the disruptive, and potentially dangerous, consequences of seizures. In many cases, medication is required for extended periods of time, and in some cases, a patient must continue to take prescription drugs for life. Furthermore, drugs used for the management of epilepsy have side-effects associated with prolonged usage, and the cost of the drugs can be considerable.

It has been postulated that free amino acids play a role in the normal functioning of the central nervous system. Amino acid concentrations in the brain specifically depend on several factors, including tissue metabolism, blood flow, transport or exclusion at the blood brain barrier, and renal or hepatic function. As such, amino acid imbalances associated with neurological disorders are of interest and have served as the basis for a variety of investigations.

However, the findings of previous studies on amino acid imbalances in epilepsy, including those by Plum (*Journal of Neurochemistry* 1974, 23, 595–600), Mutani et al. (*Epilepsia* 1974, 15, 595–597), Crawford and Chadwick (*Epilepsy Research* 1987, 1, 328–338), Haines et al. (*Epilepsia* 1985, 26, 642–648), Monaco et al. (*Italian Journal of Neurological Sciences* 1994, 15, 137–14), van Gelder et al. (*Neurochemical Research* 1980, 5, 659–671), and Ferrie et al. (*Epilepsy Research* 1999, 34, 221–229), are inconsistent. In addition to methodological sources of variation, inter-study variability has been attributed to such factors as heterogeneity within the sample population being examined, circadian variation and short-term dietary amino acid intake.

Anti-epileptic medication may also contribute to inter-study variability as increases in glycine, serine and alanine, have been noted upon valproic acid administration, while increases in free and total $\beta$-aminobutyric acid, homocarosine (a conjugate of $\beta$-aminobutyric acid), $\beta$-alanine, glycine and $\beta$-aminoisobutyric acid occur upon vigabatrin administration. Alternatively, administration of carbamazepine, ethosuximide and mephobarbital leads to decreases in leucine, proline and phenylalanine, respectively.

SUMMARY OF THE INVENTION

The present invention exploits the discovery, described herein, that amounts of uracil and thymine metabolites, especially $\beta$-aminoisobutyric acid, in various bodily fluids, especially urine, are correlated with the occurrence of epilepsy when compared to matched control subjects. Analytical and diagnostic protocols, including a novel high performance liquid chromatography system, for use in the invention are disclosed.

Reported experiments with $\beta$-alanine in animals relate to exploiting its neuro-inhibitory effects, e.g. studying how it mitigates the extent or threshold of seizure when co-administered with a drug substance known to cause seizures. It has not been previously recognized, however, that imbalances of endogenous $\beta$-alanine may be indicative of susceptibility to seizure, especially idiopathic seizures or epilepsy, familial history, and seizures resulting from head trauma. The present method may be used with noninvasive (e.g. urine collection) or minimally invasive techniques (e.g. blood collection). The method of the invention may be used to analyze neuro-active molecules such as amino acids in the urine of subjects.

In particular, the invention relates to methods of diagnosis of convulsive conditions or susceptibility thereto in a subject, wherein a bodily fluid from a subject is analyzed for the presence of a neuro-active molecule associated with a convulsive condition, and the subject is diagnosed as at risk of a convulsive condition or susceptibility thereto if the amount of the compound indicates a likelihood of same in the subject. Preferred neuro-active molecules include metabolites of uracil and thymine, particularly $\beta$-amino acids, preferably $\beta$-aminoisobutyric acid.

Furthermore, the invention relates to methods of modulating, including inhibiting or preventing, the onset of a convulsive condition in a subject, wherein a bodily fluid from a subject is analyzed for the presence of a neuro-active molecule associated with a convulsive condition; determining from the amount of the compound in the bodily fluid whether the subject is at risk of a convulsive condition; and treating the subject, if at risk of a convulsive condition, to modulate the onset of the convulsive condition in the subject. Preferred neuro-active molecules include metabolites of uracil and thymine, particularly β-amino acids, preferably β-aminoisobutyric acid.

Additionally, a method of quantifying neuro-active molecules such as β-alanine or β-aminoisobutyric acid is described, comprising collecting and optionally deproteinizing a bodily fluid sample, e.g. urine, derivatizing the amino acids present in the (deproteinized) sample, and analyzing the (derivatized) amino acids by chromatography (such as reversed phase high performance liquid chromatography), the chromatography system comprising a column, mobile phases (preferably acetate buffer and methanol), an optional internal standard (preferably D,L-ethionine) and a set of external standards of varying concentration, and a separation program which produces a resolution for each of the neuro-active molecules of interest with all other amino acids and molecules present in the bodily fluid of equal to or greater than one.

BRIEF DESCRIPTION OF THE DRAWINGS

FIG. 2 shows a representative chromatogram depicting the elution profile for a 100 μmol/L standard mixture of 23 amino acids according to a method of the invention.

DETAILED DESCRIPTION OF THE INVENTION

Figure 1:
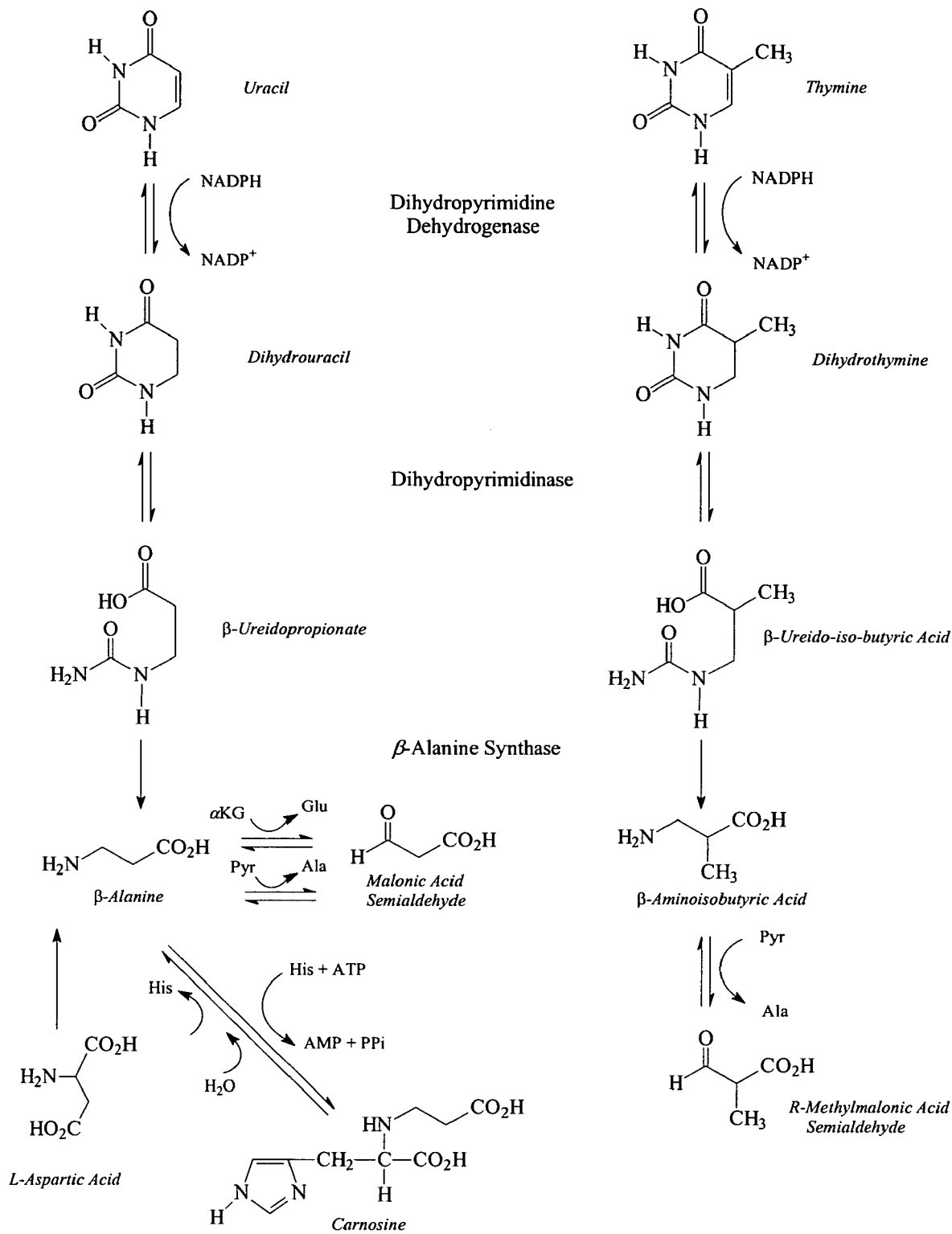
FIG. 1 illustrates various metabolic pathways implicated in the medical conditions described herein and related to β-alanine and β-aminoisobutyric acid.

The present invention entails a method of diagnosing a convulsive condition or susceptibility thereto in a subject comprising the steps of analyzing a bodily fluid from a subject for the presence or amount(s) of one or more neuro-active molecule(s), or the relative amounts of neuro-active molecules (e.g. ratio), associated with a convulsive condition; and diagnosing the subject as at risk of a convulsive condition or susceptibility thereto if the amount of said compound indicates a likelihood of same in said subject. Said subject need not have actually developed seizures.

According to the invention, a standard against which the above measure or measures from test bodily fluids are compared may be data obtained from a data bank corresponding to currently accepted normal levels of neuro-active molecules under analysis. In situations such as those where standard data are not available, the methods of the invention may further comprise conducting corresponding analyses in a second set of one or more biological samples known not to be at risk of a convulsive condition or susceptibility thereto. Such additional biological samples could be obtained, for example, previously from the subject under consideration, or from unaffected members of the public.

According to the methods of the invention, the comparison of the above measure or measures may be a straightforward comparison, such as a ratio, or it may involve weighting of one or more of the measures, relative to, for example, their importance to the particular situation under consideration. The comparison may also involve subjecting the measurement data to any appropriate statistical analysis. In most diagnostic procedures in accordance with the invention, one or more biological samples obtained from an individual will be subjected to a battery of analyses in which any number of neuro-active molecules are sought to be detected. In any such diagnostic procedure it is possible that one or more of the measures obtained will render an inconclusive result; accordingly, data obtained from a battery of measures is likely to provide for a more conclusive diagnosis. It is for this reason that an interpretation of the data based on an appropriate weighting scheme or statistical analysis is desirable.

The term "convulsive disorder" or "convulsive condition" according to the invention includes conditions wherein a subject suffers from convulsions. Convulsive disorders include, but are not limited to, epilepsy, ictogenesis, epileptogenesis, and non-epileptic convulsions, and convulsions due to administration of a convulsive agent or trauma to the subject.

A seizure is a single discrete clinical event caused by an excessive electrical discharge from a collection of neurons through a process termed "ictogenesis." As such, a seizure is merely the symptom of epilepsy.

Epilepsy is a dynamic and often progressive process characterized by an underlying sequence of pathological transformations whereby normal brain is altered, becoming susceptible to recurrent seizures through a process termed "epileptogenesis." While it is believed that ictogenesis and epileptogenesis have certain biochemical pathways in common, the two processes are not identical.

Ictogenesis (the initiation and propagation of a seizure in time and space) is a rapid and definitive electrical/chemical event occurring over seconds or minutes. Epileptogenesis (the gradual process whereby normal brain is transformed into a state susceptible to spontaneous, episodic, time-limited, recurrent seizures, through the initiation and maturation of an "epileptogenic focus") is a slow biochemical or histological process which generally occurs over months to years.

Epileptogenesis is a two phase process: Phase 1 epileptogenesis is the initiation of the epileptogenic process prior to the first seizure, and is often the result of stroke, disease (e.g. meningitis), or trauma, such as an accidental blow to the head or a surgical procedure performed on the brain. Phase 2 epileptogenesis refers to the process during which a brain that is already susceptible to seizures, becomes still more susceptible to seizures of increasing frequency or severity. While the processes involved in epileptogenesis have not been definitively identified, some researchers believe that up-regulation of excitatory coupling between neurons, mediated by N-methyl-D-aspartate (NMDA) receptors, is involved. Other researchers implicate down-regulation of inhibitory coupling between neurons, mediated by γ-aminobutyric acid (GABA) receptors, pre- or post-synaptically.

The term "subject" includes animals susceptible to convulsive disorders, epileptogenesis or capable of suffering from epileptogenic-associated states, such as warm-blooded animals, more preferably a mammal, including, e.g. non-human animals such as rats, mice, cats, dogs, sheep, horses, cattle, in addition to humans. In a preferred embodiment, the subject is a human. Subjects with a family history of convulsive conditions, a history of cerebral hypoxia or ischemia, intracranial hemorrhage, central nervous system infection or disease, drug or alcohol withdrawal, fever, trauma, brain tumor, cerebrovascular disease, metabolic disorder, degenerative central nervous system disease, drug or alcohol addiction or use, uremia, hepatic dysfunction, hypoglycemia, epilepsy, or seizure are preferred subjects for analysis according to the invention because they may be at risk for convulsions. Additionally, preferred subjects include those who have recently been administered an antibiotic, anesthetic, analgesic, immunomodulatory, psychotropic, sedative, radiographic contrast-enhancing, stimulant or hallucinogenic drug. A particularly preferred subject according to the invention is one who has suffered a head trauma and is at risk of developing post-traumatic epilepsy (PTE).

A seizure or convulsion, which terms may be used interchangeably herein, may be complex partial, simple partial, absence, secondary generalized tonic clonic, primary generalized tonic clonic, myoclonic, or atonic.

"Bodily fluid" as used herein includes, e.g., urine, blood, blood serum, amniotic fluid; cerebrospinal (i.e. CSF) and spinal fluid, synovial fluid, conjunctival fluid, salivary fluid, vaginal fluid, stool, seminal fluid, lymph, bile, tears, and sweat. A bodily fluid is advantageously CSF, urine, or blood or its components parts, e.g. plasma. A particularly preferred bodily fluid is urine.

"Neuro-active molecules" according to the invention include neurotransmitters, such as amino acid neurotransmitters, neutrostimulators, and neurodepressants. Such neuro-active molecules may alter the ability of a nerve cell to depolarize or to release or take up neurotransmitter molecules. As described herein, preferred neuro-active molecules of the invention include metabolites of uracil or thymine, especially β-amino carboxylic acids (comprising at least the sub-structure N—C—C—(C═O)—O) such as β-alanine and β-aminoisobutyric acid, and derivatives thereof. Such derivatives may be esters or other bioconjugates (including glucuronic acid and sterol conjugates).

The invention relates to convulsive conditions related to thymine or uracil metabolism, including abnormalities thereof, and therefore the compounds depicted in FIG. 1 are neuro-active molecules according to the invention as described further herein below.

"Analyzing" as used herein may be any step which either qualitatively or quantitatively indicates the amount or presence of a neuro-active molecule. Examples of analyses of the present invention include chromatography (including high-performance liquid chromatography, thin layer chromatography, or gas chromatography), spectroscopy, spectrometry, and colorimetry (such as by use of a color-changing indicator as in, for example, a "dip stick" or "test strip" as commonly used in the detection of glucose in urine), although other functional equivalents may be employed.

An analysis step may include further steps of preparing a sample for study, such as removal of interfering compounds (i.e. non-neuro-active molecules) from the bodily fluid by such means as precipitation, filtration, and the like. Additionally, neuro-active molecules may be derivatized prior to analysis to facilitate detection. For example, in analysis protocols where detection is by absorption, it may be advantageous to covalently attach a chromophore to the neuro-active molecules.

The present invention also relates to a method of modulating the onset of a convulsive condition in a subject comprising the steps of analyzing a bodily fluid from a subject at risk of a convulsive condition for the presence of a neuro-active molecule associated with a convulsive condition; determining from the amount of said compound in said bodily fluid whether said subject is at risk of a convulsive condition; and treating said subject, if at risk of a convulsive condition, to modulate the onset of said convulsive condition in said subject.

"Modulating" means altering the likelihood that a seizure will occur. Generally, modulating will mean reducing or inhibiting the likelihood of a future seizure in a subject in accordance with the invention. Modulating may refer to any convulsive condition or a precursor thereof.

The terms "treatment," "treating," or "treat," include the administration of an agent (e.g. an anticonvulsive or anti-epileptogenic, prophylactic or therapeutic pharmaceutical composition) to a subject, who has a disease or disorder, a symptom of a disease or disorder, or is at risk of suffering from the disease or disorder in the future, such that the disease or disorder (or at least one symptom of the disease or disorder) is cured, healed, prevented, alleviated, relieved, altered, remedied, ameliorated, improved or otherwise affected, preferably in an advantageous manner. "Agents" include anti-convulsive, anti-seizure, or anti-epileptogenic agents, such as described in U.S. Pat. No. 6,306,909 B1. Such a treatment step may comprise administering an effective amount of an anti-convulsive, anti-seizure, or anti-epileptogenic pharmaceutical composition.

The language "effective amount" of a compound is that amount necessary or sufficient to treat or prevent a particular condition, e.g., to prevent the various morphological and somatic symptoms of an epileptogenic-associated state. The effective amount can vary depending on such factors as the size and weight of the subject, the type of condition, or the particular agent. For example, the choice of the pharmaceutical composition can affect what constitutes an "effective amount." One of ordinary skill in the art would be able to study the aforementioned factors and make the determination regarding the effective amount of the pharmaceutical composition without undue experimentation.

The term "anti-epileptogenic agent" includes agents which are capable of inhibiting epileptogenesis, e.g., suppressing the uptake of synaptic GABA (e.g., blocking GABA transporters, e.g. GAT-1, GAT-2 or GAT-3), depressing glutamatergic excitation (e.g., interacting with an NMDA receptor, e.g. at the strychnine-insensitive glycine co-agonist site), binding to a GABA receptor (e.g. $GABA_A$), altering (e.g., increasing or suppressing) the metabolism of GABA (e.g., via inhibition of GABA transaminase).

Further examples of pharmaceutical compositions of the present invention include carbamazepine, clobazam, diazepam, lamotrigine, lorazepam, oxazepam, phenobarbital, phenyloin, primidone, valproate, ethosuximide, topirimate, felbamate, clonazepam, clobazam, nitrazepam, vigabatrin, gabapentin, levetiracetam, or tiagabine, or other pharamceuticals approved for the treatment of seizures or epilepsy by government regulatory agencies (such as the United States Food & Drug Administration), or combinations thereof.

Generally, a convulsive condition is selected from the group consisting of epileptogenic associated disorders, epileptogenesis, and non-epileptic convulsions. Inhibiting epileptogenesis includes both partial and complete reversal of epileptogenesis. Inhibiting epileptogenesis includes prevention of epileptogenesis or a decrease or slowing in the rate of epileptogenesis (e.g. a partial or complete stop in the rate of epileptogenic transformation of the brain or central nervous system tissue). It also includes any inhibition or slowing of the rate of the biochemical processes or events which take place during Phase 1 or Phase 2 epileptogenesis and lead to epileptogenic changes in tissue, i.e., in tissues of the central nervous system (CNS), e.g. the brain. Examples of processes in pathways associated with epileptogenesis are discussed in more detail herein. Modulating epileptogenesis also includes the prevention, slowing, halting, or reversing the process of epileptogenesis, i.e., the changes in brain chemistry which result in epileptic seizures.

The term "epileptogenic-associated disorders" includes disorders of the central and peripheral nervous system which may advantageously be treated as described in, e.g. U.S. Pat. No. 6,306,909 B1 and PCT publication WO 98/40,055. In an advantageous embodiment, the nervous system disorders are disorders associated with or related to the process or the results of epileptogenic transformation of the brain or other nervous tissue.

Examples of epileptogenic-associated disorders include epilepsy, head trauma, stroke, multiple sclerosis, amyotrophic lateral sclerosis, psychoses, cerebral ischemia, motor neuron disease, Alzheimer's disease, encephalitis (including encephalitis arising from chicken-pox, measles or pertussis), infections of the CNS (meningitis, encephalitis), subdural haematoma, brain tumour, and birth defects including anoxic brain injury, dementia and other disorders (in humans or animals) in which altered activity of neurotransmitters is a cause, at least in part, of the disorder (see, e.g. Schoepp et al., *Eur. J. Pharmacol.* 1991, 203, 237–243; Leeson et al., *J. Med. Chem.* 1991, 34, 1243–1252; Kulagowski et al., *J. Med. Chem.* 1994, 37, 1402–1405; Mallamo et al., *J. Med. Chem.* 1994, 37, 4438–4448; and references cited therein). The term epileptogenic-associated disorders includes both convulsive disorders and disorders associated with NMDA receptor activity.

The invention also relates to particular novel methods of analysis, including a method of quantifying neuro-active molecules, such as β-alanine or β-aminoisobutyric acid, comprising the steps of collecting a bodily fluid sample, such as urine; optionally deproteinizing said sample; optionally derivatizing the neuro-active molecules present in said (deproteinized) sample; and analyzing said (derivatized) neuro-active molecules by chromatography, said chromatography system comprising a column (preferably a reversed phase C8 or C18 column), mobile phases (preferably acetate buffer and methanol), an optional internal standard (preferably D,L-ethionine) and a set of external standards of varying concentration, and a separation program which produces a resolution for derivatized neuroactive molecule(s) of interest present in said sample of equal to or greater than one. This method is most advantageously applied to the analysis of amino acid neuro-active molecules, particularly β-aminoisobutyric acid or another metabolite of uracil or thymine.

The analysis method may further comprise a step of deproteinizing said bodily fluid, for example by ultrafiltration, ultracentrifugation, or chemical precipitation. The chemical precipitation step may employ a precipitating agent, for example, sulfosalicylic acid, perchloric acid, trichloroacetic acid, picric acid, acetonitrile, ethanol, acetone, or methanol.

The derivatizing step may covalently attach a chromophore to an amino acid, and preferred reagents for use in such a derivatizing step include o-phthalaldehyde, 9-fluorenylmethylchloroformate, phenyl isothiocyanate, or 1-dimethylaminonaphthalene-5-sulphonyl chloride, as well as other commercially available reagents.

In this invention, levels of β-aminoisobutyric acid are correlated with the occurrence of epilepsy, as demonstrated by the following, wherein the concentrations of β-alanine and its metabolic equivalent β-aminoisobutyric acid in urine collected from subjects with epilepsy and matched control subjects were studied. A novel reversed-phase high performance liquid chromatography (RP-HPLC) program is disclosed for the analytical separation and quantification of β-alanine and β-aminoisobutyric acid in urine.

Protein in physiological fluids is typically inevitable, but it interferes with amino acid analysis and shortens the lifetime of chromatographic columns. Several methods have been proposed for the removal of protein from physiological fluids, including chemical precipitation, ultrafiltration, and ultracentrifugation, with chemical precipitation finding the most frequent use. Sulfosalicylic acid is a common precipitation agent, and is used as a solution in distilled de-ionized water in concentrations as high as 20% (w/v). This methodology does, however, tend to lower the concentrations of aspartic acid and glutamic acid in solution due to their decreased solubility under strongly acidic conditions. Once precipitation is complete, the sample is filtered, making it ready for derivatization and analysis.

With a few exceptions, free amino acids cannot be detected using experimental techniques such as UV absorption. A variety of methods known in the art are therefore available for the derivatization of amino acids prior to analytical separation and detection by RP-HPLC. Generally, pre-column derivatization is preferred, as it results in increased resolution and sensitivity over the corresponding post-column methodology. With derivatization using o-phthalaldehyde (OPA), 9-fluorenylmethyl chloroformate (FMOC—Cl), phenyl isothiocyanate (PITC) or 1-dimethylaminonaphthalene-5-sulphonyl chloride (dansyl-Cl), the automated OPA method is generally the most amenable to routine analysis of primary amino acids except cysteine.

With the OPA method, primary amino acids are reacted with o-phthalaldehyde in the presence of the reducing agent β-mercaptoethanol. Detection of the corresponding derivatized amino acid is achieved by the monitoring of absorbance at a wavelength of 340 nm. This reaction occurs in a 1:1:1 ratio, with the elimination of two molecules of water, to yield the corresponding fluorescent 1-alkylthio-2-alkyl-substituted isoindoles. OPA is inherently non-fluorescent and as such gives low reagent interference. The derivatization reaction is rapid and occurs readily at ambient temperature. Typically, detection limits lie in the low picomole range. Disadvantages, however, include the instability of the fluorescent isoindoles, the inability to detect secondary amino acids such as proline and hydroxyproline, and the poor fluorescent response arising from the derivatization of a few amino acids, in particular cysteine.

Several modifications may improve the sensitivity and reproducibility of this reaction as well as the stability of its products. The addition of BRIJ-35 (polyoxyethylene lauryl ether (ICI Americas)) enhances the fluorescent response of lysine and hydroxylysine. Alternative thiol containing reagents, such as tert-butyl thiol, also increase the stability of the corresponding isoindoles. The reproducibility of the derivatization reaction can be enhanced through the maintenance of constant reaction times and temperatures, e.g. via automated derivatization at temperature-controlled conditions. Finally, avoiding the use of excess o-phthalaldehyde reagent minimizes the degradation of the isoindole intermediate, which improves the sensitivity of quantitative amino acid analysis.

Traditionally, analytical separation and detection of amino acids in physiological fluids involved ion-exchange chromatography in combination with post-column ninhydrin derivatization and subsequent detection using either spectrophotometry or colorimetry. However, the advantage of reduced analysis times, improved resolution and enhanced sensitivity, along with the development of HPLC has prompted a shift away from this classical method of amino acid analysis. Several manual and automated RP-HPLC procedures using o-phthalaldehyde derivatization have since been developed for the separation and detection of amino acids in physiological fluids, but very few have been specifically designed for the detection and quantification of β-alanine and β-aminoisobutyric acid.

Metabolic pathways involving β-alanine and β-aminoisobutyric acid are depicted in FIG. 1. As illustrated in this FIG. 1, β-alanine and β-aminoisobutyric acid are believed to be endogenously derived via the metabolism of uracil and thymine, respectively.

The first of three enzymes involved in this pathway is dihydropyrimidine dehydrogenase. This enzyme is responsible for catalyzing the reversible NAPDH-dependent conversion of uracil and thymine to dihydrouracil and dihydrothymine. This initial step is rate determining with respect to the overall breakdown of uracil and thymine to β-alanine and β-aminoisobutyric acid.

Further transformation of these metabolites, through the action of dihydropyrimidinase, reversibly yields β-ureidopropionate and β-ureido-iso-butyric acid.

Finally, β-alanine synthase, also referred to as β-ureidopropionase or N-carbamoyl-β-alanine amidohydrolase, facilitates the irreversible hydrolytic cleavage of β-ureidopropionate and β-ureido-iso-butyric acid to give β-alanine and β-aminoisobutyric acid as well as the release of ammonia ($NH_3$) and carbon dioxide ($CO_2$). This enzyme is of particular importance in animals in that it is directly responsible for the in vivo biosynthesis of β-alanine, with its action occurring predominantly in the liver. It is the R-isomer of β-aminoisobutyric acid that is formed via this reaction. The corresponding S-isomer is generated through the metabolism of L-valine.

Minor sources of β-alanine arise from the actions of two enzymes, aspartate decarboxylase, found in bacteria of the intestinal lumen which decarboxylates aspartic acid to give β-alanine; and carnosinase, which catabolizes carnosine to give β-alanine and histidine.

Dihydropyrimidine dehydrogenase is the rate-limiting enzyme in the catabolic pathway from uracil and thymine to β-alanine and β-aminoisobutyric acid. A deficiency of this enzyme has deleterious physiological effects. Dihydropyrimidine dehydrogenase deficiency results from the autosomal recessive inheritance of a mutant allele coding for the dihydropyrimidine dehydrogenase enzyme (Gonzales, et al., *T.I.P.S.* 1995, 16, 325–327). The presence of this mutation leads to the loss of a 165 base pair exon, resulting in the expression of truncated mRNA. This mutation can lead to a drop in enzyme activity by as much as 98 to 100%.

Dihydropyrimidine dehydrogenase deficiency has two distinct clinical forms (Scriver, et al., *The Metabolic and Molecular Bases of Inherited Disease;* 7 ed.; Scriver, et al., Eds.; McGraw-Hill, Inc.: New York, 1995; Vol. 1). The genetic form, involving an inborn error of metabolism, is an early onset disorder commonly associated with neurological signs such as seizures, impaired cognitive development, hypertonia, hyperreflexia, microcephaly and dysmyelination. The iatrogenic form, which occurs following exposure to the cancer chemotherapeutic agent 5-fluorouracil, is characterized by clinical symptoms such as encephalopathy, neurotoxicity and neutropenia. Withdrawal of this drug eliminates all symptoms of this disorder (Tuchman, et al., *New Eng. J. Med.* 1985, 313, 245–249).

The pathophysiology underlying the association of epilepsy with dihydropyrimidine dehydrogenase deficiency remains unclear. It has, however, been suggested that seizure etiology may arise at the level of the nucleic acids (Braakhekke, et al., *J. Neuro. Sci.* 1987, 78, 71–77). Uridine, a pyrimidine nucleoside, has been shown to exhibit anticonvulsant activity in animal models of epilepsy. Atypical regulation of uridine and its related compounds may therefore be important in explaining abnormal central nervous system regulation. A correlation between the lack of β-alanine and the neurological symptoms of dihydropyrimidine dehydrogenase deficiency has also been suggested.

Since its initial detection, several cases of dihydropyrimidine dehydrogenase deficiency have been documented (van Gennip, et al., *Adv. Exp. Med. Biol.* 1989, 253A, 111–118). Diagnosis of this disorder is normally based on presence of high levels of uracil, thymine and 5-hydroxymethyluracil (a metabolite of thymine), in physiological fluids (Valik, et al., *Mayo Clin. Proc.* 1997, 72, 719–725; van Gennip, et al., *Clin. Chem.* 1993, 39, 380–385). In urine, uracil and thymine levels can be elevated by as much as one hundred fold for the iatrogenic form and one thousand fold for the genetic form. Definitive diagnosis of this disorder does, however, require conclusive proof of an enzyme deficiency. To quantify dihydropyrimidine dehydrogenase activity, cultured fibroblasts are first incubated with 14C-thymine. The loss of 14C-thymine and the formation of 14C-dihydrothymine are then quantified using a combination of HPLC and liquid scintillation counting to give a measure of enzyme activity (Bakkeren, et al., *Clin. Chim. Acta* 1984, 140, 247–256).

Dihydropyrimidinuria is a disorder resulting from a deficiency in dihydropyrimidinase, the second of three enzymes along the catabolic pathway from uracil and thymine to β-alanine and β-aminoisobutyric acid. Excretion of large quantities of dihydrouracil and dihydrothymine are therefore associated with this condition. Although it is believed to be autosomal recessive, little else is known about this disorder. Only two cases of dihydropyrimidinuria have been reported. One subject exhibited convulsions, lowered consciousness and metabolic acidosis, while the other showed signs of gross microcephaly, spastic quadriplegia, choreiform movements and severe developmental retardation (Webster, et al., *The Metabolic and Molecular Bases of Inherited Disease;* 7 ed.; Scriver, et al., Eds.; McGraw-Hill, Inc.: New York, 1995; Vol. 2).

Catabolism of β-alanine primarily occurs through the actions of two aminotransferases, β-alanine-α-ketoglutarate transaminase and β-alanine-pyruvate transaminase, and results in the production of malonic acid semialdehyde. It is a deficiency of the former enzyme that is believed to underlie hyper-β-alaninemia, a rare disorder characterized by increased levels of β-alanine and GABA in cerebrospinal fluid, plasma and urine as well as β-aminoisobutyric acid in urine (Scriver, et al., *New Eng. J. Med.* 1966, 274, 635–643). This postulate is supported by three key observations. First, the administration of pyridoxine, whose derivative pyridoxal-5-phosphate acts as an aminotransferase coenzyme, has been effective in the symptomatic treatment of hyper-β-alaninemia. Second, β-alanine, S-β-aminoisobutyric acid, and GABA are all transaminated with β-ketoglutarate via the actions of these transaminases in both the brain and liver. Finally, the fact that both β-alanine and GABA are elevated in physiological fluids suggests a lack of involvement of β-alanine-pyruvate transaminase, whose substrate specificity is for β-alanine alone.

Only two cases of hyper-β-alaninemia have been reported to date. One subject exhibited somnolence and repeated grand-mal seizures and died within five months of birth, while the other was described as having intermittent generalized tonic-clonic seizures, lethargy and Cohen's syndrome (Higgins, et al., *Neurology* 1994, 44, 1728–1732). The etiology of these neurological symptoms remains unclear. Plausible explanations include the inhibition of GABA transaminase by excess β-alanine, competitive binding of β-alanine to the GABA receptor, as well as agonism of the strychinine-sensitive glycine and NMDA receptors by β-alanine.

Hyper-β-aminoisobutyric aciduria is a reasonably prevalent disorder involving a deficiency in β-aminoisobutyrate-pyruvate transaminase, an enzyme responsible for the catabolism of β-aminoisobutyric acid. Subjects with this disorder typically exhibit less than 10% of the normal enzyme activity and therefore excrete large quantities of this amino acid. The genetic variant of this disorder is postulated to be recessive, stemming from a genetic polymorphism at a single locus. This trait appears to have a nonrandom distribution within the population, with highest frequencies in the Micronesian population and lowest frequencies in the Caucasian population.

Other factors are known to influence the excretion of β-aminoisobutyric acid. Children are known to have higher excretion rates than adults, while females tend to have higher excretion rates than males. Enhanced excretion of β-aminoisobutyric acid is also a factor to be considered with neoplastic states and with Down's syndrome as well as during periods of increased somatic cell growth, when pyrimidine turnover is significantly elevated.

Therefore, a variety of neuro-active molecules, such as amino acids, including β-alanine, β-aminoisobutyric acid, and those compounds depicted in FIG. 1 are within the scope of the present invention.

The invention described herein is exemplified by the following non-limiting method. Other analytical methods known in the art may be employed according to the teachings herein. The method described below may be modified by one skilled in the art using no more than routine experimentation. Such functionally equivalent analytical methods are also encompassed by the instant invention.

HPLC-grade methanol and HPLC-grade glacial acetic acid were obtained from Fisher Scientific (Fair Lawn, N.J.), sodium acetate was obtained from Sigma-Aldrich (Milwaukee, Wis.) and fluoraldehyde reagent solution was obtained from Pierce Chemical (Rockford, Ill.). Individual L-amino acids, β-alanine, β-aminoisobutyric acid, D,L-ethionine and sulfosalicylic acid were also obtained from Sigma-Aldrich.

A System Gold liquid chromatographic system was combined with a Model 125 programmable solvent module fitted with an Altex 210A injection valve, a Model 166 programmable UV-VIS detector module (Beckman, San Ramon, Calif.); a Dell 489P/33 computer and an Epson FX-870 printer. A 5 μm Ultrasphere ODS column (250 mm×4.6 mm I.D.) with a 5 μm Ultrasphere ODS guard column (45 mm×4.6 mm I.D.), both from Beckman, were used. Solvents were filtered through 0.22 μm nylon filters (NO2SPO4700) from Osmonics (Minnetonka, Minn., U.S.A.). Distilled de-ionized water was prepared using a Culligan de-ionizer from Structural Fibers (Chardon, Ohio).

Human subjects with epilepsy and matched control subjects were sub-classified into the following five groups:

Epilepsy Groups: E+D+) subjects whose seizure frequency per month was greater than zero (mean average seizure frequency per month 1.23; range 0.2–4) over the past six months prior to sample collection and who were taking anti-epileptic medication (8 male and 7 female), E–D+) subjects whose seizure frequency per month was zero over the past six months prior to sample collection and who were taking anti-epileptic medication (13 male and 9 female), and E–D–) subjects whose seizure frequency per month was zero over the past six months prior to sample collection and who were not taking anti-epileptic medication (9 male and 3 female).

Control Groups: C–D+) subjects without a prior history of seizures and who were taking anti-epileptic medication (18 male and 6 female) and C–D–) subjects without a prior history of seizures and who were not taking anti-epileptic medication (22 male and 5 female).

For those subjects with epilepsy, the etiology of seizures was infection (chicken-pox, measles encephalitis, pertussis encephalitis, viral encephalitis, viral meningitis) for 8 subjects, trauma (subdural hematoma) for 2 subjects, birth complications (anoxic brain injury) for 11 subjects, central nervous system defects (cerebral cortical atrophy with hydrocephalus, congenital brain abnormality with hydrocephalus, spastic quadriplegia, spina bifida with hydrocephalus) for 7 subjects, prenatal complications (maternal congenital rubella, maternal eclampsia) for 2 subjects, miscellaneous (fetal complications due to hyperemesis graviderum, Rett syndrome) for 2 subjects and unknown for 17 subjects.

Subjects with epilepsy in groups E+D+ and E–D+ as well as matched control subjects in group C–D+ were receiving various combinations of anti-epileptic medication including carbamazepine, clobazam, diazepam, lamotrigine, lorazepam, oxazepam, phenobarbital and phenyloin. Eleven subjects with epilepsy (30%) and 21 control subjects (88%) were taking only one medication, 14 subjects with epilepsy (38%) and three matched control subjects (12%) were taking two medications, 10 subjects with epilepsy (27%) were taking three medications, while 2 subjects with epilepsy (5%) were taking four medications.

Subjects with one of primary generalized epilepsy (absence seizures), chromosomal abnormalities (fragile X syndrome, Down's syndrome, and Angelman's happy puppet syndrome) or amino acid disorders (phenylketonuria, amino aciduria) were excluded, as were subjects receiving the anti-epileptic medication vigabatrin.

A single urine sample was collected from each subject in the study population between the hours of 6:00 and 11:00 am on the morning following a meatless dinner. In this way, it was anticipated that sample variability arising from circadian variation as well as the influence of diet on uracil concentrations might be minimized. Samples were screened for leukocytes, nitrite, pH, protein, glucose, ketones, urobilinogen, bilirubin and blood using a CHEM 9 Chemstrip Urine Test Strip from Boehringer Mannheim (Indianapolis, Ind., U.S.A). All samples used in this study fell within normal reference ranges for the aforementioned criteria. Each sample was separated into three aliquots and placed in separate labeled disposable vials. Samples were cooled to 0–4° C. for transport. For long-term storage, samples were kept at −50 to −60° C.

A stock solution of β-alanine and β-aminoisobutyric acid was prepared by dissolving each compound in distilled de-ionized water to a final concentration of 0.1 mmol/L. Working external standards were prepared from the stock solution by dilution with distilled de-ionized water to final concentrations of 1, 5, 10, 20, 40, 60, 80, 100, 200, 400, and 600 μmol/L. A stock solution of D,L-ethionine, the internal standard, was prepared by dissolving it in distilled de-ionized water to a final concentration of 1 mmol/L. A stock solution of 23 amino acids was prepared by dissolving each compound in distilled de-ionized water to a final concentration of 1 mmol/L. Stock solutions of the individual L-amino acids were prepared to final concentrations ranging from 30 μmol/L to 2.5 mmol/L. The standard amino acid mixture was used for method development while individual L-amino acid standards were used for peak identification. For long-term storage, all standards were kept at −50° C. to −60° C.

Urine samples were deproteinized via chemical precipitation using sulfosalicylic acid according to the following procedure, although other deproteinization procedures as known in the art may also be employed.

Urine samples were thawed and vortex mixed for 30 sec. In a disposable tube, 100 μL 15% (w/v) sulfosalicylic acid was added to 1 mL of sample. The resulting mixture was vortex mixed and left standing for 5 min. The treated sample was filtered through a disposable 5" P.P. chromatography column fitted with a medium (45–90 μm) filter from DiaMed Lab Supplies (Mississauga, ON, Canada) into a second disposable tube. Deproteinization led to urine sample dilution by a factor of 1.10.

Fluoraldehyde reagent solution, containing o-phthalaldehyde (0.8 mg/mL, purchased from Pierce Chemical Co., Rockford, Ill.), β-mercaptoethanol and BRIJ-35, in a borate buffer (pH ~10), was used for the derivatization of primary amino acids in urine samples and standards according to the following procedure: In an ice bath, 10 μL of 1 mmol/L D,L-ethionine (internal standard) was added to 30 μL of a sample, external standard or blank (distilled de-ionized water) in a disposable tube. The resulting solution was vortex mixed for 10 sec. To this was added 20 μL of fluoraldehyde reagent solution and the resulting solution was vortex mixed for 20 sec. After 1 min, 80 μL of 0.1 mmol/L sodium acetate buffer (pH=7.0) was added and the solution was vortex mixed for 20 sec. The derivatized solution was loaded onto the injection loop and 20 μL was injected at 2 min.

RP-HPLC was used to separate and detect the presence of amino acids in urine. Eluent A (50 mmol/L sodium acetate buffer, pH 5.7) and eluent B (methanol) were degassed by vacuum filtration through a nylon filter (0.22 um). The upper and lower pressure limits were set at 4.00 and 0.00 kPSI. For all samples and standards, the injection volume was 20 μL. Elution was performed at ambient temperature at a flow rate of 1.5 mL/min with the concentration of eluent B as follows: 0–16 min, isocratic elution at 30%: 16–21 min, linear gradient from 30–36%: 21–28 min, isocratic elution at 36%: 28–32 min, linear gradient from 36–55%: 32–35 min, isocratic elution at 55%: 35–38 min, linear gradient from 55–70%: 38–48 min isocratic elution at 70%. The absorbance of the column eluate was monitored at a wavelength of 340 nm. The integration parameters, peak threshold and peak width, were set at $3.9 \times 10^{-4}$ and 0.48, respectively. The column was washed and reconditioned with the concentration of eluent B as follows: 48–51 min, linear gradient from 70–100%: 51–56 min, isocratic elution at 100%: 56–59 min, linear gradient from 100–30%: 59–69 min, isocratic elution at 30%. Total analysis time per sample was 48 min, while total analysis time between samples was 69 min.

The RP-HPLC procedure was optimized to ensure maximal and reproducible separation of a 23 amino acid mixture with respectable resolution of taurine, β-alanine, β-aminoisobutyric acid and β-aminobutyric acid. A representative chromatogram depicting the elution profile for a 100 μmol/L standard mixture of 23 amino acids is illustrated in FIG. 2.

Urinary creatinine concentrations were quantified and used to standardize amino acid results for the sample population with respect to renal clearance. β-Alanine and β-aminoisobutyric acid concentrations were expressed as ratios relative to the concentrations of creatinine in their respective samples.

TABLE 1

Levels of β-alanine and β-aminoisobutyric acid in urine from subjects with epilepsy.

| Subject | β-Alanine[a] (μmol/mmol Creatinine) | β-Aminoisobutyric Acid[a] (μmol/mmol Creatinine) |
|---|---|---|
| 1 | 1.400 | 41.85 |
| 2 | 0.5799 | 39.72 |
| 3 | 1.411 | 11.80 |
| 4 | 2.061 | 10.63 |
| 5 | 1.220 | 16.95 |
| 6 | 0.8061 | 5.660 |
| 7 | 7.092 | 101.2 |
| 8 | 0.1816 | 10.35 |
| 9 | 1.751 | <0.3310 |
| 10 | <0.2967 | 34.80 |
| 11 | 4.061 | 125.3 |
| 12 | 2.217 | 28.31 |
| 13 | 1.371 | 30.29 |
| 14 | 4.160 | 6.415 |
| 15 | <0.1312 | 7.183 |
| 16 | 1.852 | 42.52 |
| 17 | 5.307 | 75.77 |
| 18 | 2.465 | 16.19 |
| 19 | 1.080 | 9.256 |
| 20 | 1.143 | 7.380 |
| 21 | <0.3580 | 9.930 |
| 22 | 3.587 | 140.1 |
| 23 | 0.9659 | 345.7 |
| 24 | 0.9704 | 7.048 |
| 25 | 1.017 | 18.57 |
| 26 | 14.39 | 43.09 |
| 27 | 2.464 | 9.337 |
| 28 | 0.4409 | 13.98 |
| 29 | 1.495 | 42.77 |
| 30 | 1.233 | 71.01 |
| 31 | 0.7048 | 16.58 |
| 32 | 2.008 | 42.58 |
| 33 | 11.06 | 12.75 |
| 34 | 3.926 | 15.36 |
| 35 | 5.954 | 23.07 |
| 36 | 0.6052 | 3.428 |
| 37 | 0.2621 | 19.11 |
| 38 | 0.8235 | 20.79 |
| 39 | 0.3032 | 3.030 |
| 40 | 2.453 | 45.99 |
| 41 | 1.471 | 36.96 |
| 42 | 0.4948 | 20.76 |
| 43 | 2.568 | 81.94 |
| 44 | 0.6136 | 13.77 |
| 45 | 2.502 | 17.58 |
| 46 | 10.28 | 40.65 |
| 47 | 1.042 | 143.6 |
| 48 | 1.127 | 6.014 |
| 49 | 0.4841 | 4.322 |
| Mean[b] | 2.509 | 38.07 |
| Median[b] | 1.406 | 18.07 |
| Standard Deviation[b] | 2.970 | 56.92 |
| Confidence Interval[b,c] | 1.624–3.394 | 32.80–43.34 |

[a]Values for β-alanine and β-aminoisobutyric acid are expressed as a ratio of the amino acid concentration, measured in units of μmol/L, against creatinine, measured in units of mmol/L.
[b]Values in which the concentration of β-alanine or β-aminoisobutyric acid fell below the limit of detection were not included in the calculation.
[c]Confidence intervals were calculated at the 95% confidence level.

TABLE 2

Levels of β-alanine and β-aminoisobutyric acid in urine from a matched control group.

| Subject | β-Alanine[a] (μmol/mmol Creatinine) | β-Aminoisobutyric Acid[a] (μmol/mmol Creatinine) |
|---|---|---|
| 1 | 0.2763 | 4.567 |
| 2 | 10.44 | 9.216 |
| 3 | 0.4764 | 3.560 |
| 4 | 4.736 | 11.44 |
| 5 | 0.7618 | 6.124 |
| 6 | 19.38 | 9.079 |
| 7 | <0.1075 | 8.300 |
| 8 | 1.573 | 37.08 |
| 9 | 0.7881 | 9.435 |
| 10 | 6.375 | 8.064 |
| 11 | 0.4085 | 12.92 |
| 12 | 1.403 | 7.159 |
| 13 | 3.122 | 12.92 |
| 14 | 0.2249 | 8.300 |
| 15 | 1.662 | 21.04 |
| 16 | 0.8533 | 3.811 |
| 17 | 0.7743 | 8.101 |
| 18 | 0.1502 | 7.979 |
| 19 | 1.806 | 60.68 |
| 20 | 0.6231 | 18.14 |
| 21 | 2.518 | 16.99 |
| 22 | 0.3880 | 36.44 |
| 23 | 2.921 | 46.43 |
| 24 | <0.05104 | 4.627 |
| 25 | 0.4782 | 8.229 |
| 26 | 2.480 | 5.205 |
| 27 | 0.5029 | 21.74 |
| 28 | 1.248 | 22.37 |
| 29 | 15.27 | 14.16 |
| 30 | 0.4514 | 3.354 |
| 31 | 43.41 | 25.95 |
| 32 | 0.9628 | 31.99 |
| 33 | 12.44 | 9.725 |
| 34 | 11.31 | 21.30 |
| 35 | 0.2259 | 3.219 |
| 36 | 0.2200 | 37.65 |
| 37 | 3.418 | 14.43 |
| 38 | 0.4532 | 26.93 |
| 39 | 0.6999 | 10.26 |
| 40 | 0.04266 | 18.26 |
| 41 | 0.1145 | 6.350 |
| 42 | <0.1147 | 2.176 |
| 43 | 1.822 | 3.131 |
| 44 | 0.7089 | 4.340 |
| 45 | 0.1500 | 20.69 |
| 46 | 1.390 | 6.114 |
| 47 | 0.7200 | 38.42 |
| 48 | 2.612 | 15.40 |
| 49 | 8.350 | 15.50 |
| 50 | <0.07333 | 9.588 |
| 51 | 8.901 | 68.91 |
| Mean[b] | 2.916 | 16.43 |
| Median[b] | 8.533 | 10.26 |
| Standard Deviation[b] | 4.390 | 14.63 |
| Confidence Interval[b,c] | 1.626–4.206 | 12.29–20.57 |

[a]Values for β-alanine and β-aminoisobutyric acid are expressed as a ratio of amino acid concentration, measured in units of μmol/L, against creatinine, measured in units of mmol/mL.
[b]Values in which the concentration of β-alanine or β-aminoisobutyric acid fell below the limit of detection were not included in the calculation.
[c]Confidence intervals were calculated at the 95% confidence level.

Nonparametric statistical analysis was used to assess the statistical significance of differences in urinary β-amino acid concentrations observed between subjects with epilepsy and matched control subjects. Using a two-tailed Mann-Whitney test with a normal approximation, a significant difference for β-aminoisobutyric acid ($Zc=2.40$, $0.01<P<0.02$) was found between subjects with epilepsy and matched control subjects.

The corresponding one-tailed tests showed that levels of β-aminoisobutyric acid were higher for those subjects with epilepsy ($Zc=2.40$, $0.005<P<0.01$). Significant differences in β-alanine and β-aminoisobutyric acid concentrations were not observed when comparing male subjects with epilepsy to female subjects with epilepsy (β-alanine $U=338$; β-aminoisobutyric acid $U=354$) as well as when comparing male subjects in the control population to female subjects in control population (β-alanine $U=229$; β-aminoisobutyric acid $U=267$). These results show that gender does not influence the statistical significance of the observed differences in urinary β-amino acid concentrations between subjects with epilepsy and matched control subjects.

Using a Mann-Whitney test with a normal approximation, significant differences in urinary β-aminoisobutyric acid concentrations ($Zc=2.37$, $0.01<P<0.02$) were determined upon comparing male subjects with epilepsy to male matched control subjects. Based on the corresponding one-tailed Mann-Whitney test, these levels were statistically higher for those male subjects with epilepsy ($Zc=2.37$, $0.005<P<0.01$).

Using a Krusal-Wallis test with a chi-square approximation, significant differences in the urinary levels of β-alanine and β-aminoisobutyric acid were not detected between subgroups E+D+, E−D+ and E−D− of the population with epilepsy (β-alanine $Hc=0.585$; β-aminoisobutyric acid $H=0.266$). Nor were differences determined between subgroups C−D+ and C−D− of the control population, using a two-tailed Mann-Whitney test with a normal approximation (β-alanine $Zc=0.387$; β-aminoisobutyric acid $Zc=0.670$).

These results show that seizure frequency and anticonvulsant medication do not affect the statistical significance of the observed differences in urinary β-amino acid concentrations. A comparison of subjects with epilepsy in groups E+D+ and E−D+, receiving anticonvulsant medication, to matched control subjects in the group C−D−, not receiving anticonvulsant medication, demonstrated a significant difference for β-aminoisobutyric acid ($Zc=2.08$, $0.02<P<0.05$), with higher levels of this amino acid occurring in the urine of these subjects with epilepsy ($Zc=2.08$, $0.01<P<0.025$).

Similarly, a comparison of subjects with epilepsy in groups E+D+ and E−D+, receiving anticonvulsant medication, to matched control subjects in the group C−D+, also receiving anticonvulsant medication, demonstrated significant differences in β-aminoisobutyric acid levels ($Zc=2.06$, $0.02<P<0.05$). β-Aminoisobutyric acid concentrations were again found to be statistically higher for these subjects with epilepsy, as determined by a one-tailed Mann-Whitney test with a normal approximation ($Zc=2.06$, $0.01<P<0.025$). These results show that significant differences in urinary β-aminoisobutyric acid concentrations are not influenced by anticonvulsant medication alone.

The decision to analyze urine rather than cerebrospinal fluid (CSF) or plasma was taken after careful consideration. It has long been appreciated that the chemical milieu of the CSF provides information regarding abnormal cerebral metabolism. CSF is not, however, a mere ultrafiltrate formed by the choroids plexus, but arises from the interactions between blood and the CNS (Perry, et al., Clin. Invest. 1961, 40, 1363–1372). These interactions permit many substances, especially amino acids, to exhibit similar levels in plasma as well as in CSF.

Scriver et al. in their studies of people with hyper-β-alaninemia, clearly demonstrated that the increased levels of β-alanine in the CSF are directly reflected in plasma (op. cit.). They also noted a direct relationship between plasma levels and urinary excretion, attributing this observation to the renal tubular transport of β-amino acids. Urinary levels of β-alanine therefore provide a window of observation into the metabolism of β-alanine within the CNS.

From an analytical point of view, urine analysis is preferred as the control range for β-aminoisobutyric acid in adult urine is substantially higher when compared to plasma or CSF (β-aminoisobutyric acid=10–510 μmol/L for urine, 0 μmol/L for plasma, <10 nmol/L for CSF). Urine also represents an easily accessible biological fluid in which to collect from the brain-injured individual.

To validate the notion of screening for seizure susceptibility based on urinary levels of β-alanine and β-aminoisobutyric acid, the sensitivity and specificity of this assay were calculated at defined β-amino acid concentrations. Optimal results were achieved when the cut-offs for seizure susceptibility were set at concentrations of 0.8 μmol/mmol creatinine for β-alanine and 10 μmol/mmol creatinine for β-aminoisobutyric acid in urine samples, although useful clinical data may be obtained at other cut-off values. The skilled artisan will appreciate that such cut-off levels may be different for other bodily fluids. For β-aminoisobutyric, the sensitivity of this assay, defined as the probability of testing positive for seizure susceptibility when a susceptibility is truly present, was determined to be 73%, while the specificity, defined as the probability of testing negative for seizure susceptibility when no susceptibility exists, was 47%

In summary, the results indicate that subjects with seizure disorders excrete more aminoisobutyric acid in their urine than people who do not have seizure disorders. Urinary levels of these amino acids were statistically higher for the 49 subjects with epilepsy relative to the 51 matched control subjects. Statistical differences are not significantly influenced by gender, administration of anticonvulsant medication, or seizure frequency. Accordingly urinary concentrations of β-alanine and β-aminoisobutyric acid may be used as biological markers for seizure presence and susceptibility and epileptogenesis.

The potential clinical applications of measurements of urinary β-alanine and β-aminoisobutyric acid levels are multiple. First, such an assay may assist in verifying the presence of epilepsy. Differentiating seizures from nonepileptic seizures (psuedoseizures) is a common clinical problem. Urinary β-aminoisobutyric acid levels augment clinical observation, EEG studies and serum prolactin measurements as useful clinical tools in the differentiation between epileptic and nonepileptic seizures. Secondly, a urinary assay for β-aminoisobutyric acid has utility in predicting seizure susceptibility. Seizures may arise from a diversity of CNS insults, including trauma, infection, ischaemia, and neoplasia. Identifying which subset of patients will ultimately develop recurrent seizures after such an insult is currently an unattainable clinical goal. The predictive test described herein to identify those with a predisposition to epilepsy therefore has significant clinical value.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims. The contents of all references, issued patents, and published patent applications cited throughout this application are hereby incorporated by reference.

What is claimed is:

1. A method of diagnosing a convulsive condition or susceptibility thereto in a subject comprising the steps of
   analyzing a urine from a subject for the presence or amount of a β-amino acid, or the relative amount of a β-amino acid; and
   diagnosing the subject as at risk of a convulsive condition when the amount of said β-amino acid indicates a likelihood of same in said subject,
   wherein said β-amino acid is β-alanine or β-aminoisobutyric acid, and wherein said diagnosing step is positive when the concentration of said β-alanine is greater than 0.8 μmol/mmol creatinine or said β-aminoisobutyric acid is greater than 10 μmol/mmol creatinine.

2. The method of claim 1, wherein said convulsive condition is selected from the group consisting of epileptogenic associated disorders, epileptogenesis, and non-epileptic convulsions.

3. The method of claim 1, wherein said convulsive condition is an epileptogenic-associated disorder selected from the group consisting of epilepsy, head trauma, stroke, multiple sclerosis, amyotrophic lateral sclerosis, psychosis, cerebral ischemia, motor neuron disease, Alzheimer's disease, chicken-pox, measles, pertussis encephalitis, infections of the central nervous system(CNS), meningitis, encephalitis, subdural haematoma, brain tumour, birth defects, anoxic brain injury dementia, and other disorders in which altered activity of neuro-active molecules is a cause, at least in part, of the disorder.

4. The method of claim 1, wherein said convulsive condition is selected from the group consisting of epilepsy and non-epileptic convulsions.

5. The method of claim 1, wherein said subject has not yet developed seizures.

6. The method of claim 1, further comprising a step of deproteinizing said bodily fluid prior to analyzing the bodily fluid.

7. The method of claim 6, wherein said deproteinizing step is ultrafiltration, ultracentrifugation, or chemical precipitation.

8. The method of claim 7, wherein said chemical precipitation step employs sulfosalicylic acid, perchloric acid, trichloroacetic acid, picric acid, acetonitrile, ethanol, acetone, or methanol.

9. The method of claim 1, further comprising a step of derivatizing said amino acid prior to analyzing it.

10. The method of claim 9, wherein said derivatizing step covalently attaches a chromophore to said amino acid.

11. The method of claim 9, wherein said derivatizing step employs o-phthalaldehyde, 9-fluorenylmethylchloroformate, phenyl isothiocyanate, or 1-dimethylaminonaphthalene-5-sulphonyl chloride.

12. The method of claim 1, wherein said subject is an animal or human.

13. The method of claim 12, wherein said subject has a family history of convulsive conditions, a history of cerebral hypoxia or ischemia, intracranial hemorrhage, central nervous system infection or disease, drug or alcohol withdrawal, fever, trauma, brain tumor, cerebrovascular disease, metabolic disorder, degenerative central nervous system disease, drug or alcohol addiction or use, uremia, hepatic dysfunction, hypoglycemia, epilepsy, or seizure; or said subject has recently been administered an antibiotic, anesthetic, analgesic, immunomodulatory, psychotropic, sedative, antihistamine, radiographic contrast-enhancing, stimulant or hallucinogenic drug.

14. The method of claim 13, wherein said seizure is selected from the group consisting of complex partial, simple partial, absence, secondary generalized tonic clonic, primary generalized tonic clonic, myoclonic, and atonic.

15. The method of claim 1, wherein said subject has suffered a head trauma.

16. The method of claim 15, wherein said convulsive condition is post-traumatic epilepsy (PTE) or a susceptibility thereto.

17. The method of claim 1, wherein the analyzing step comprises chromatography, spectroscopy, spectrometry, or colorimetry.

18. The method of claim 17, wherein said chromatography is high-performance liquid chromatography, thin layer chromatography, or gas chromatography.

19. The method of claim 1, wherein the analyzing step comprises a method of quantifying said β-alanine or said β-aminoisobutyric acid comprising the steps of collecting a urine sample;

deproteinizing said urine sample;

derivatizing the amino acids present in said deproteinized urine sample; and analyzing said derivatized amino acids by high performance liquid chromatography, said high performance liquid chromatography comprising a reversed phase column, acetate buffer and methanol mobile phases, an internal standard, and a separation program which produces a resolution for each of said β-alanine or said β-aminoisobutyric acid with all other amino acids and molecules present in said urine of equal to or greater than one.

20. The method of claim 19, wherein said internal standard is D,L-ethionine.

21. The method of claim 20, wherein said reversed phase column is an $C_8$ or $C_{18}$ column.

* * * * *